US005780286A

United States Patent [19]
Dillon et al.

[11] Patent Number: 5,780,286
[45] Date of Patent: Jul. 14, 1998

[54] ARGINASE II

[75] Inventors: Patrick J. Dillon, Gaithersburg, Md.; Joseph G. Vockley, Downingtown, Pa.

[73] Assignees: SmithKline Beecham Corporation, Philadelphia, Pa.; Human Genome Sciences Inc., Rockville, Md.

[21] Appl. No.: 700,186

[22] Filed: Aug. 20, 1996

Related U.S. Application Data

[60] Provisional application No. 60/013,395, Mar. 14, 1996.

[51] Int. Cl.$^6$ ....................................................... C12N 9/78
[52] U.S. Cl. .................. 435/227; 435/172.3; 435/320.1; 435/325; 435/363; 435/348; 435/349; 435/350; 435/351; 435/352; 435/364; 435/365; 435/366; 435/254.11; 435/252.3; 536/23.2; 935/9; 935/14; 935/10; 935/32; 514/44
[58] Field of Search ........................... 435/172.3, 320.1, 435/325, 363, 348, 349, 350, 351, 352, 364, 365, 366, 254.11, 252.3, 227; 536/23.2; 935/9, 14, 10, 32, 29, 28, 27, 34, 33, 52, 66

[56] References Cited

PUBLICATIONS

Cederbaum et al. 1979 Ped. Res. 13:827–833.
Cederbaum et al. 1977 J. Ped. 90(4):569–573.
Dizikes et al. 1986 Biochem. Biophys. Res. Commun. 141(1):53–59.
Grody et al. 1993 Hum Genet. 91:1–5.
Grody et al. 1989 J. Clin. Invest. 83:602–609.
Michels et al. 1978 Clin. Genet. 13:61–67.
Spector et al. 1983 Ped Res. 17(12):941–944.
Am. J. Hum. Genet. (Suppl.) 55(3): A139, Sep. 1994, Program and Meeting Abstracts—1994 Annual Meeting.
Gotoh et al. 1996 FEBS Lett. 395:119–122.
Jenkinson et al. 1996 Comp. Biochem. Physiol. 114B(1):107–132.
Vockley et al. 1996 Genomics 38:118–128.
Baker et al. 1982 in: Th Study of Biology, Fourth Edition, Addison–Wesley Publ. Co., Reading, MA (p. 9).
Entrez (ver. 7.0) released OctobTO8457, ISSN 1065–707X, National Centr for Biotechnology Information.
Adams et al. 1993 Nature Genetics 4:373–380.

*Primary Examiner*—Christopher S. F. Low
*Attorney, Agent, or Firm*—William T. Han; William T. King; Edward T. Lentz

[57] ABSTRACT

The invention relates to Arginase II polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

16 Claims, 10 Drawing Sheets

ESTs forming the Arginase II contig

| EST # | cDNA Library |
|---|---|
| 1 | Jurkat T-cell |
| 2 | Human colon |
| 3 | Human stromal cell line |
| 4 | Jurkat T-cell |
| 5 | Human prostate BPH |
| 6 | Human prostate hyperplasia |
| 7 | LNCAP (prostate cancer cell line) |
| 8 | Human colon |
| 9 | Human brain |
| 10 | Human colon adenocarcinoma |
| 11 | Human testis tumor |
| 12 | Human stromal cell line |
| 13 | Human stromal cell line |
| 14 | Human prostate cancer |
| 15 | Human prostate cancer |
| 16 | Human prostate cancer |
| 17 | Human pineal gland |
| 18 | Human pineal gland |
| 19 | Human prostate cancer |
| 20 | Human synovium |
| 21 | Human synovium |

FIG. 1B

```
      gganctctgccttggagattctcagtgctgcggatcATGTCCCTAAGGGGCAGCCTCTCG
  3   -------+---------+---------+---------+---------+---------+--  62
      cctngagacggaacctctaagagtcacgacgcctagTACAGGGATTCCCCGTCGGAGAGC

G  ?  L  P  W  R  F  S  V  L  R  I  M  S  L  R  G  S  L  S   -

CGTCTCCTCCAGACGCGAGTGCATTCCATCCTGAAGAAATCCGTCCACTCCGTGGCTGTG
 63   -------+---------+---------+---------+---------+---------+--  122
      GCAGAGGAGGTCTGCGCTCACGTAAGGTAGGACTTCTTTAGGCAGGTGAGGCACCGACAC

R  L  L  Q  T  R  V  H  S  I  L  K  K  S  V  H  S  V  A  V   -

ATAGGAGCCCCGTTCTCACAAGGGCAGAAAAGAAAAGGAGTGGAGCATGGTCCCGCTGCC
123   -------+---------+---------+---------+---------+---------+--  182
      TATCCTCGGGGCAAGAGTGTTCCCGTCTTTTCTTTTCCTCACCTCGTACCAGGGCGACGG

I  G  A  P  F  S  Q  G  Q  K  R  K  G  V  E  H  G  P  A  A   -

ATAAGAGAAGCTGGCTTGATGAAAAGGCTCTCCAGTTTGGGCTGCCACCTAAAAGACTTT
183   -------+---------+---------+---------+---------+---------+--  242
      TATTCTCTTCGACCGAACTACTTTTCCGAGAGGTCAAACCCGACGGTGGATTTTCTGAAA

I  R  E  A  G  L  M  K  R  L  S  S  L  G  C  H  L  K  D  F   -

GGAGATTTGAGTTTTACTCCAGTCCCCAAAGATGATCTCTACAACAACCTGATAGTGAAT
243   -------+---------+---------+---------+---------+---------+--  302
      CCTCTAAACTCAAAATGAGGTCAGGGGTTTCTACTAGAGATGTTGTTGGACTATCACTTA

G  D  L  S  F  T  P  V  P  K  D  D  L  Y  N  N  L  I  V  N   -

CCACGCTCAGTGGGTCTTGCCAACCAGGAACTGGCTGAGGTGGTTAGCAGAGCTGTGTCA
303   -------+---------+---------+---------+---------+---------+--  362
      GGTGCGAGTCACCCAGAACGGTTGGTCCTTGACCGACTCCACCAATCGTCTCGACACAGT

P  R  S  V  G  L  A  N  Q  E  L  A  E  V  V  S  R  A  V  S   -

GATGGCTACAGCTGTGTCACACTGGGAGGAGACCACAGCCTGGCAATCGGTACCATTAGT
363   -------+---------+---------+---------+---------+---------+--  422
      CTACCGATGTCGACACAGTGTGACCCTCCTCTGGTGTCGGACCGTTAGCCATGGTAATCA

```
     GGCCATGCCCGACACTGCCCAGACCTTTGTGTTGTCTGGGTTGATGCCCATGCTGACATC
423  ------+---------+---------+---------+---------+---------+--- 482
     CCGGTACGGGCTGTGACGGGTCTGGAAACACAACAGACCCAACTACGGGTACGACTGTAG

G  H  A  R  H  C  P  D  L  C  V  V  W  V  D  A  H  A  D  I  -

AACACACCCCTTACCACTTCATCAGGAAATCTCCATGGACAGCCAGTTTCATTTCTCCTC
483  ------+---------+---------+---------+---------+---------+--- 542
     TTGTGTGGGGAATGGTGAAGTAGTCCTTTAGAGGTACCTGTCGGTCAAAGTAAAGAGGAG

N  T  P  L  T  T  S  S  G  N  L  H  G  Q  P  V  S  F  L  L  -

AGAGAACTACAGGATAAGGTACCACAACTCCCAGGATTTTCCTGGATCAAACCTTGTATC
543  ------+---------+---------+---------+---------+---------+--- 602
     TCTCTTGATGTCCTATTCCATGGTGTTGAGGGTCCTAAAAGGACCTAGTTTGGAACATAG

R  F  L  Q  D  K  V  P  Q  L  P  G  F  S  W  I  K  P  C  I  -

TCTTCTGCAAGTATTGTGTATATTGGTCTGAGAGACGTGGACCCTCCTGAACATTTTATT
603  ------+---------+---------+---------+---------+---------+--- 662
     AGAAGACGTTCATAACACATATAACCAGACTCTCTGCACCTGGGAGGACTTGTAAAATAA

S  S  A  S  I  V  Y  I  G  L  R  D  V  D  P  P  E  H  F  I  -

TTAAAAGGAACTATGGATATCCAGTATTTTTTCCATGGAGGAGATATTGGATCGAACTTG
663  ------+---------+---------+---------+---------+---------+--- 722
     AATTTTCCTTGATACCTATAGGTCATAAAAAAGGTACCTCCTCTATAACCTAGCTTGAAC

L  K  G  T  M  D  I  Q  Y  F  F  H  G  G  D  I  G  S  N  L  -

GTATCCAGGAAGGTCATGGGAACGGAACATTTGATCTGGCTGATTGGCAAGAGACAAAGA
723  ------+---------+---------+---------+---------+---------+--- 782
     CATAGGTCCTTCCAGTACCCTTGCCTTGTAAACTAGACCGACTAACCGTTCTCTGTTTCT

V  S  R  K  V  M  G  T  E  H  L  I  W  L  I  G  K  R  Q  R  -

CCAATCCATTTGAGTTTTGATATTGATGCATTTGACCCTACACTGGCTCCAGCCACAGGA
783  ------+---------+---------+---------+---------+---------+--- 842
     GGTTAGGTAAACTCAAAACTATAACTACGTAAACTGGGATGTGACCGAGGTCGGTGTCCT

P  I  H  L  S  F  D  I  D  A  F  D  P  T  L  A  P  A  T  G  -

ACTCCTGTTGTCGGGGGACTAACCTATCGAGAAGGCATGTATATTGCTGAGGAAATACAC
843  ------+---------+---------+---------+---------+---------+--- 902
     TGAGGACAACAGCCCCCTGATTGGATAGCTCTTCCGTACATATAACGACTCCTTTATGTG

T  P  V  V  G  G  L  T  Y  R  E  G  M  Y  I  A  E  E  I  H  -

AATACAGGGTTGCTATCAGCACTGGATCTTGTTGAAGTCAATCCTCAGTTGGCCACCTCA
903  ------+---------+---------+---------+---------+---------+--- 962
     TTATGTCCCAACGATAGTCGTGACCTAGAACAACTTCAGTTAGGAGTCAACCGGTGGAGT

```
         GAGGAAGAGGCGAAGACTACAGCTAACCTGGCAGTAGATGTGATTGCTTCAAGCTTTGGT
   963   --------+---------+---------+---------+---------+---------+-- 102
         CTCCTTCTCCGCTTCTGATGTCGATTGGACCGTCATCTACACTAACGAAGTTCGAAACCA

E   E   E   A   K   T   T   A   N   L   A   V   D   V   I   A   S   S   F   G  -

CAGACAAGAGAAGGAGGGCATATTGTCTATGACCAACTTCCTACTCCCAGTTCACCAGAT
  1023   --------+---------+---------+---------+---------+---------+-- 108
         GTCTGTTCTCTTCCTCCCGTATAACAGATACTGGTTGAAGGATGAGGGTCAAGTGGTCTA

Q   T   R   E   G   G   H   I   V   Y   D   Q   L   P   T   P   S   S   P   D  -

GAATCAGAAAATCAAGCACGTGTGAGAATTTAG
  1083   --------+---------+---------+-----
         CTTAGTCTTTTAGTTCGTGCACACTCTTAAATC

| Primer Sequence | Location | Seq ID No. |
|---|---|---|
| 1F 5'-ATGTCCCTAAGGGGCAGCCTCTCGCGTC-'3 | 1 | 3 |
| 1R 5'-TAAATTCTCACACGTGCTTGATTTTCTG-'3 | 1075 | 4 |
| 2F 5'-CTCTGCCTTGGAGATTCTCAGTGCTGCGGA-'3 | 30 | 5 |
| 2R 5'-ATTGTCTCCTAAATTCTCACACGTGCTTGA-'3 | 2005 | 6 |
| 3F 5'-GAGGTGCTTAGCAGAGCTGTGTCAGAT-'3 | 301 | 7 |
| 3R 5'-CAACAGGAGTTCCTGTGGCTGG-'3 | 814 | 8 |
| 4F 5'-GCTGATTGGCAAGAGACAAAGACCAATCCA-'3 | 723 | 9 |
| 4R 5'-GGGCATGGCCACTAATGGTACCGATTGCC-'3 | 395 | 10 |
| 5F 5'-GATTGCCTTATGGAATTCATGTCCCCTAAGGGGCAGCCTCTCGCGTC-'3 | -9 | 11 |
| 5R 5'-GATTGCCTTCTGCAGTAAATTCTCACACGTGCTTGATTTTCTG-'3 | 1090 | 12 |
| 6F 5'-AGGAACTATGGATAT-'3 | 630 | 13 |
| 6R 5'-CTTGCCAATCTGCCT-'3 | 734 | 14 |
| 7F 5'-ATGTGATTGCTTCAAGCTTTG-'3 | 962 | 15 |

FIG. 3

1 ATGTCCCTAAGGGGCAGCCTCTCGCGTCTCCTCCAGACGCGAGTGCATTC 50
          |    ||| | ||  |  |   ||| ||     |      |
1 ....TCACTGAGGGTTGACTGACTGGAGAGCTCAAGTGCAGCAAAGAGAA 46

51 CATCCTGAAGAAATCCGTCCACT......CCGTGGCTGTGATAGGAGCCC 94
       | ||  |     || | | |        || | |   | ||  |||||| |
47 GTGTCAGAGCATGAGCGCCAAGTCCAGAACCATAGGGATTATTGGAGCTC 96

95 CGTTCTCACAAGGGCAGAAAAGAAAAGGAGTGGAGCATGGTCCCGCTGCC 144
   | |||||| | || ||| | || ||| |||||| | || ||   | |
97 CTTTCTCAAAGGGACAGCCACGAGGAGGGTGGAAGAAGGCCCTACAGTA 146

145 ATAAGAGAAGCTGGCTTGATGAAAAGGCTCTCCAGTTTGGGCTGCCACCT 194
     | ||| | ||||| || | |  ||            |  ||  |  |
147 TTGAGAAAGGCTGGTCTGCTTGAGAAACTTAAAGAACAAGAGTGTGATGT 196

195 AAAAGACTTTGGAGATTTGAGTTTTACTCCAGTCCCCAAAGATGATCTCT 244
    || || |  ||| || ||  |||  ||   ||||  || ||   || ||
197 GAAGGATTATGGGGACCTGCCCTTTGCTGACATCCCTAATGACAGTCCCT 246

245 ACAACAACCTGATAGTGAATCCACGCTCAGTGGGTCTTGCCAACCAGGAA 294
    | |  ||      ||||||| | || |||||    || | | || |
247 TTCAAATTGTGA...AGAATCCAAGGTCTGTGGGAAAAGCAAGCGAGCAG 293

295 CTGGCTGAGGTGGTTAGCAgAGCTGTGTCAGATGGCTACAGCTGTGTCAC 344
    |||||||   |||     ||    |    | ||    | ||   |
294 CTGGCTGGCAAGGTGGCACAAGTCAAGAAGAACGGAAGAATCAGCCTGGT 343

345 ACTGGGAGGAGACCACAGCCTGGCAATCGGTACCATTAGTGGCCATGCCC 394
    |||||  |||||||||| ||||||  || | |||     ||||||||||

FIG. 4A

```
344 GCTGGGCGGAGACCACAGTTTGGCAATTGGAAGCATCTCTGGCCATGCCA 393

395 GACACTGCCCAGACCTTTGTGTTGTCTGGGTTGATGCCCATGCTGACATC 444
     |   |||  || ||| | || ||||||| ||||| ||  |||| |||
394 GGGTCCACCCTGATCTTGGAGTCATCTGGGTGGATGCTCACACTGATATC 443

445 AACACACCCCTTACCACTTCATCAGGAAATCTCCATGGACAGCCAGTTTC 494
    ||||| || || || || ||    |||||  | ||||||| || || ||
444 AACACTCCACTGACAACCACAAGTGGAAACTTGCATGGACAACCTGTATC 493

495 ATTTCTCCTCAGAGAACTACAGGATAAGGTACCACAACTCCCAGGATTTT 544
     || ||||| |  ||||||  |  ||| | ||  |  | |||||||| |
494 TTTCCTCCTGAAGGAACTAAAAGGAAAGATTCCCGATGTGCCAGGATTCT 543

545 CCTGGATCAAACCTTGTATCTCTTCTGCAAGTATTGTGTATATTGGTCTG 594
    |||||  | || || ||||| |||  |      ||||||||||||| ||
544 CCTGGGTGACTCCCTGTATATCTGCCAAGGATATTGTGTATATTGGCTTG 593

595 AGAGACGTGGACCCTCCTGAACATTTTATTTTAAAAGGAACTATGGATAT 644
    |||||||||||||||  ||||| | ||||| |||             ||
594 AGAGACGTGGACCCTGGGGAACACTACATTTTGAAAACTCTAGGCATTAA 643

645 CCAGTATTTTTTCCATGGAGGAGATATTGgATCGAACTTGGTATCCAGGA 694
     | ||   |  || || || ||            |   |   |   | |
644 ATACTTTTCAATGACTGAAGTGGA.........CAGACTAGGAATTGGCA 684

695 AGGTCATGgGAACGGAACATTTGATCTGGCTGATTGGCAAGAGACAAAGA 744
    ||||  ||| |   ||| |  || | ||  ||| | |   |    ||||
```

FIG. 4B

```
685 AGGTGATGGAA...GAAACACTCAGCTATCTACTAGGAAGAAAGAAAAGG 731

745 CCAATCCATTTGAGTTTTGATATTGATGCATTTGACCCTACACTGGCTCC 794
    ||||| ||| | |||||||||| |||| | | | ||||| | | | ||
732 CCAATTCATCTAAGTTTTGATGTTGACGGACTGGACCCATCTTTCACACC 781

795 AGCCACAGGAACTCCTGTTGTCGGGGACTAACCTATCGAGAAGGCATGT 844
    ||| || || || || || || || || || || || ||||||| | |
782 AGCTACTGGCACACCAGTCGTGGGAGGTCTGACATACAGAGAAGGTCTCT 831

845 ATATTGCTGAGGAAATACACAATACAGGGTTGCTATCAGCACTGGATCTT 894
    | || | || |||||  |||| ||||||| | || |||| | | ||| |
832 ACATCACAGAAGAAATCTACAAAACAGGGCTACTCTCAGGATTAGATATA 881

895 GTTGAAGTCAATCCTCAGTTGGCCACCTCAGAGGAAGAGGCGAAGACTAC 944
    | ||||| || ||    ||| | || ||||| | |     ||
882 ATGGAAGTGAACCCATCCCTGGGGAAGACACCAGAAGAAGTAACTCGAAC 931

945 AGCTAACCTGGCAGTAGATGTGATTGCTTCAAGCTTTGGTCAGACAAGAG 994
    || ||| ||||| |  |           | | || || |    | |
932 AGTGAACACAGCAGTTGCAATAACCTTGGCTTGTTTCGGACTTGCTCGGG 981

995 AAGGAGGGCATATTGTCTATGACCAACTTCCTACTCCCATTCACCAGATG 1044
    | ||    || |     |||| ||| | ||   | ||   |   |   |
982 AGGGTAATCACAAGCCTATTGACTACCTTAACCCACCTAAGTAAATGTGG 1031

1045 AATCAGAAAATCAAGCACGTGTGAGAATTTA.................. 1075
     |||| || |  |  |  |  |
1032 AAACATCCGATATAAATCTCATAGTTAATGGCATAATTAGAAAGCTAATC 1081
```

FIG. 4C

```
  1 ..............TEG*LTGELKCSKEKCQSMSAKSRTIGIIGAPFSKG  36
                  | |.  |...   ...  ..|..|   :::|||||.|
  1 GXLPWRFSVLRIMSLRGSLSRLLQTRVHSILKKSVHS..VAVIGAPFSQG  48

37 QPRGGVEEGPTVLRKAGLLEKLKEQECDVKDYGDLPFADIPNDSPF.QIV  85
    |.|  |||.||..:|.|||:.:|..  :|.:|||:|||.|...:|.|. : .::
 49 QKRKGVEHGPAAIREAGLMKRLSSLGCHLKDFGDLSFTPVPKDDLYNNLI  98

86 KNPRSVGKASEQLAGKVAQVKKNGRISLVLGGDHSLAIGSISGHARVHPD 135
    ||||||  |.:: ||:  |...  .:|   ::.||||||||||.|||||| ||
 99 VNPRSVGLANQELAEVVSRAVSDGYSCVTLGGDHSLAIGTISGHARHCPD 148

136 LGVIWVDAHTDINTPLTTTSGNLHGQPVSFLLKELKGKIPDVPGFSWVTP 185
    |.|:|||||.|||||||||.|||||||||||||:||.:|:|:::||||:.|
149 LCVVWVDAHADINTPLTTSSGNLHGQPVSFLLRELQDKVPQLPGFSWIKP 198

186 CISAKDIVYIGLRDVDPGEHYILK.TLGIKYF..SMTEVDRLGIGKVME. 231
    |||. .||||||||||.||:|||  |::|.||  :  . ...|.  |||:
199 CISSASIVYIGLRDVDPPEHFILKGTMDIQYFFHGGDIGSNLVSRKVMGT 248

232 ETLSYLLGRKKRPIHLSFDVDGLDPSFTPATGTPVVGGLTYREGLYITEE 281
    | | :|:|::.||||||||:|::||..:||||||||||||||||:||.||
249 EHLIWLIGKRQRPIHLSFDIDAFDPTLAPATGTPVVGGLTYREGMYIAEE 298

282 IYKTGLLSGLDIMEVNPSLGKTPEEVTRTVNTAVAITLACFGLAREGNHK 331
    |..|||||:||::|||| |:...||..  |.|  ||.:.  .:|| .|||.|
299 IHNTGLLSALDLVEVNPQLATSEEEAKTTANLAVDVIASSFGQTREGGHI 348

332 PIDYLNPPK*MWKHPI*IS*LMA*LES*SFS*A*
    ..| |  .|.                  | .  |
349 VYDQLPTPSS...........PDESENQARVRI*
```

FIG. 5

ARGINASE II

This application claims the benefit of U.S. Provisional Application Ser. No: 60/013,395, filed Mar. 14, 1996.

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human Arginase II.

BACKGROUND OF THE INVENTION

Clinically significant hyperargininemia results from mutations in the Type I arginase gene (Arginase I) (Cederbaum S. D., et al., 1979, Pediat Res 13:827–833; Cederbaum S., et al., 1977, J. Pediatr 90:569–573; Michel V. V., et al., 1978, Clin Genet 13:61–67) which is predominantly expressed in the liver and red blood cells (Gasiorowska I, et al., 1970, Biochim Biophys Acta 17:19–30; Hermann B. G. and Frischauf A-M., 1987, Meth Enzymol 152:180–183; Spector E. B., et al., 1982, Biochem Med 28:165–175.) Arginase I deficient patients present with spasticity, growth retardation, progressive mental impairment and episodic hyperammonemia (Cederbaum S. D., et al., 1979, Pediat Res 13:827–833; Cederbaum S. D., et al., 1977, J. Pediatr 90:569–573; Thomas K. R. and Capecchi M. R., 1987, Cell 51:503–512.) Although significantly devastating, Arginase I deficiency has a milder clinical phenotype than other urea cycle disorders. It has been proposed that the presence of a second isoform of arginase might be responsible for this milder presentation (Grody W. W., et al., 1989, J Clin Invest 83:602–609; Grody W. W., et al., 1993, Hum Genet 91:1–5) The existence of an extra-urea cycle form of arginase (Arginase II), which localizes to the mitochondria (Wissmann P. B., et al., 1994, Am J Hum Genet 55:A139), has been demonstrated utilizing various non-cross reacting antibodies to Arginase I and Arginase II (Spector E. B., et al., 1983, Pediatr Res 17:941–944). In patients deficient in type I arginase activity, a compensatory up regulation of Arginase II has been observed (Gasiorowska I, et al., 1970, Biochim Biophys Acta 17:19–30; Hermann B. G., et al., 1987, Meth Enzymol 152:180–183). Using these antibodies, it has been established that Arginase II is expressed predominantly in the kidney, but is also found in the brain, activated macrophage, the gastrointestinal tract and in the lactating mammary gland (Spector E. B., et al., 1983, Pediatr Res 17:941–944.) Arginase II is not expressed at a significant level in the liver or red blood cells. In addition to a hypothetical role in the production of proline and glutamate it has been postulated that Arginase II may play an important role in nitric oxide biosynthesis through the production of ornithine as a precursor of glutamate (Mezl V. A., et al., 1977, Biochem J 164:105–113; Wang W. W., et al., 1995, Biochem Biophys Res Comm 210:1009–1016.) It is because of the many potential extra-urea cycle, metabolic roles of Arginase II and its up regulation in the hyperargininemic patient, with its implications for gene therapy, that cloning of the Arginase II gene is important. Many different techniques have been utilized to isolate the gene for Arginase II. The presence of six highly conserved regions in the protein, present in the arginases of most species examined, has been critical to the discovery process (Johnson J. L., et al., 1984, J Neurochem 43:1123–1126; Ikeda Y, et al., 1987, Arch Biochem Biophys 252:662–674.)

SUMMARY OF THE INVENTION

Toward these ends, and others, it is an object of the present invention to provide polypeptides, inter alia, that have been identified as novel Arginase II by homology between the amino acid sequence set out in FIG. 2 and known amino acid sequences of other proteins such as Type I arginase and agmatinase.

It is a further object of the invention, moreover, to provide polynucleotides that encode Arginase II, particularly polynucleotides that encode the polypeptide herein designated Arginase II.

In a particularly preferred embodiment of this aspect of the invention the polynucleotide comprises the region encoding human Arginase II in the sequence set out in FIG. 2 or in the cDNA in ATCC deposit No. 75,656, deposited Jan. 26, 1994 (referred to herein as the deposited clone).

In accordance with this aspect of the invention there are provided isolated nucleic acid molecules encoding human Arginase II, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human Arginase II.

It also is an object of the invention to provide Arginase II polypeptides, particularly human Arginase II polypeptides, to treat diseases associated with or caused by a defect in the Arginase II gene or Arginase II gene expression, such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage.

In accordance with another object of the invention is a method of using Arginase II to control nitric oxide formation in an individual having a need to control such formation.

In accordance with yet another object of the invention is a method of treating systemic hypotension caused by sepsis or cytokines using Arginase II alone or in combination with an alpha sub-1 adrenergic agonist.

Another object of the invention is a method to deplete systemic arginine levels in an individual having a need for a depletion of such levels.

In accordance with this aspect of the invention there are provided novel polypeptides of human origin referred to herein as Arginase II as well as biologically, diagnostically or therapeutically useful fragments, variants and derivatives thereof, variants and derivatives of the fragments, and analogs of the foregoing.

Among the particularly preferred embodiments of this aspect of the invention are variants of human Arginase II encoded by naturally occurring alleles of the human Arginase II gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned Arginase II polypeptides comprising culturing host cells having expressibly incorporated therein an exogenously-derived human Arginase II-encoding polynucleotide under conditions for expression of human Arginase II in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing Arginase II expression in cells by determining Arginase II polypeptides of Arginase II-encoding mRNA; in a sample from a host organism having or suspected of having a disease associated with or caused by a defect in the Arginase II gene or Arginase II gene expression, such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage, in vitro, ex vivo or in vivo by exposing cells to Arginase II polypeptides or polynucleotides as disclosed herein; assaying genetic variation and aberrations, such as defects, in Arginase II genes; and administering a Arginase II polypeptide or polynucleotide to an organism to augment Arginase II function or remediate Arginase II dysfunction.

Another object of the invention is a method for the preparation of L-ornithine salts.

Yet another object of the invention is a method for the diagnosis of a disorder arising from Arginase II deficiency in an individual having or suspected of having a defect in the nitric oxide pathway and the urea cycle.

Also provided is a method to monitor progression or therapy of disorders with hypotension as a clinical sign.

Further provided is a method to monitor progression of or therapy of disorders of the immune or nervous systems associated with or caused by nitric oxide regulation.

Another object of the invention is a method to monitor activation state of macrophage.

A further object of the invention is a method to monitor mitochondrial activity as a function of the transportation of arginase II into the mitochondria.

In accordance with certain preferred embodiments of this and other aspects of the invention there are provided probes that hybridize specifically to human Arginase II sequences.

In certain additional preferred embodiments of this aspect of the invention there are provided antibodies against Arginase II polypeptides. In certain particularly preferred embodiments in this regard, the antibodies are highly selective for human Arginase II.

In accordance with another aspect of the present invention, there are provided Arginase II agonists. Among preferred agonists are molecules that mimic Arginase II, that bind to Arginase II-binding molecules or receptor molecules, and that elicit or augment Arginase II-induced responses. Also among preferred agonists are molecules that interact with Arginase II or Arginase II polypeptides, or with other modulators of Arginase II activities, and thereby potentiate or augment an effect of Arginase II or more than one effect of Arginase II.

In accordance with yet another aspect of the present invention, there are provided Arginase II antagonists. Among preferred antagonists are those which mimic Arginase II so as to bind to Arginase II receptor or binding molecules but not elicit a Arginase II-induced response or more than one Arginase II-induced response. Also among preferred antagonists are molecules that bind to or interact with Arginase II so as to inhibit an effect of Arginase II or more than one effect of Arginase II.

The agonists and antagonists may be used to mimic, augment or inhibit the action of Arginase II polypeptides. They may be used, for instance, to treat diseases associated with or caused by a defect in the Arginase II gene or Arginase II gene expression, such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage.

In a further aspect of the invention there are provided compositions comprising a Arginase II polynucleotide or a Arginase II polypeptide for administration to cells in vitro, to cells in vivo and to cells in vivo, or to a multicellular organism. In certain particularly preferred embodiments of this aspect of the invention, the compositions comprise a Arginase II polynucleotide for expression of a Arginase II polypeptide in a host organism for treatment of disease. Particularly preferred in this regard is expression in a human patient for treatment of a dysfunction associated with aberrant endogenous activity of Arginase II or to provide therapeutic. Such compositions may be used to treat, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 2A, 2B and 2C show the nucleotide (SEQ ID NO:1) and deduced amino acid (SEQ ID NO:2) sequence of human Arginase II, and are, collectively FIG. 2.

FIG. 3 shows the primers used in cloning the Arginase II cDNA.

FIGS. 4A. 4B and 4C show the regions of similarity between polynucleotide sequences of Arginase II (top) and Arginase I (bottom) polynucleotides. and are. collectively FIG. 4.

FIG. 5 shows the regions of similarity between polypeptide sequences of Arginase I (top) and Arginase II (bottom).

GLOSSARY

Figure 1A:
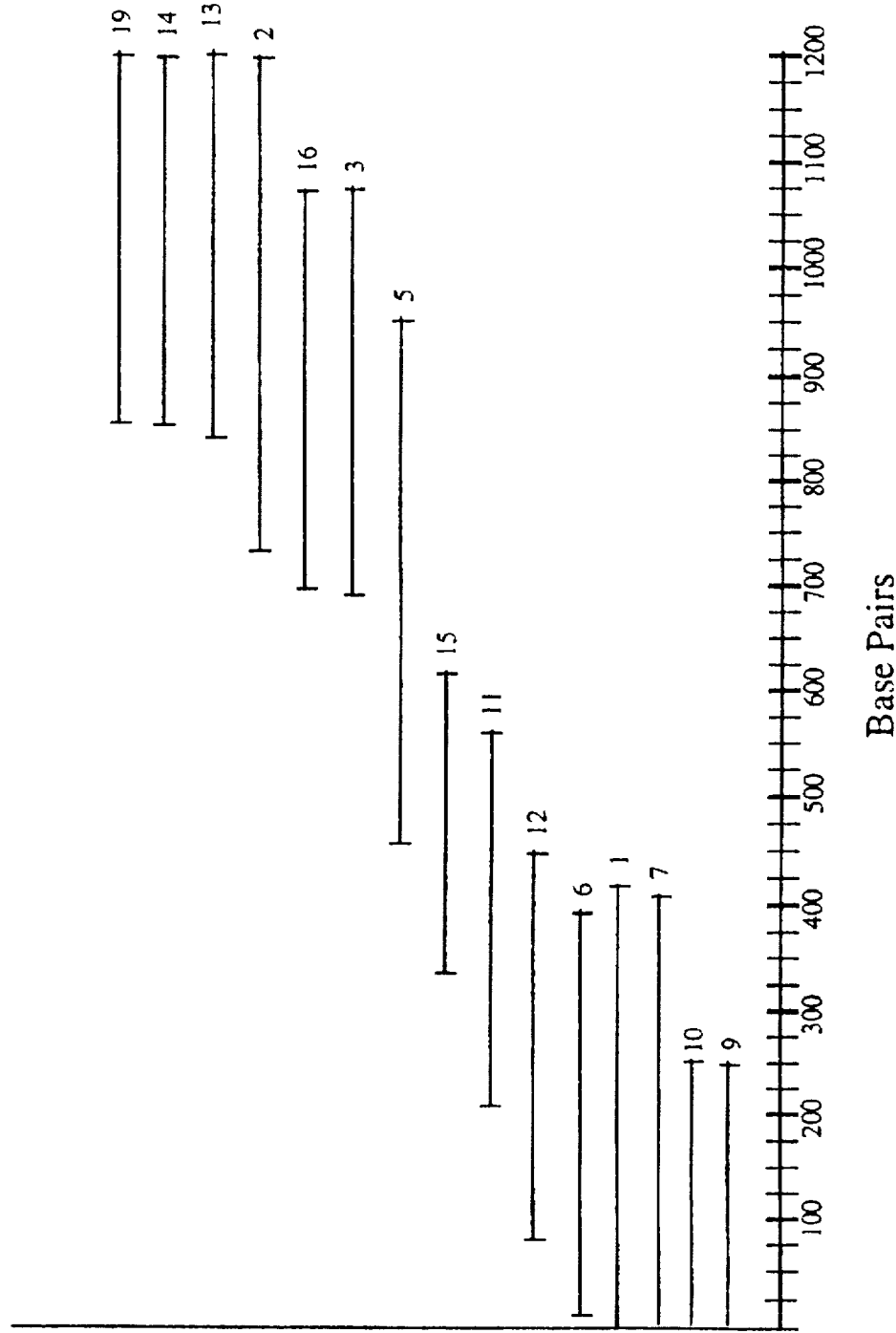
FIG. 1 (A) shows the contig of the Arginase II cDNA with the EST numbers from FIG. 1(B) aligned with the EST, and (B) shows the ESTs that form the Arginase II contig.

The following illustrative explanations are provided to facilitate understanding of certain terms used frequently herein. particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions. cofactors and other requirements for use are known and routine to the skilled artisan.

For analytical purposes. typically. 1 mg of plasmid or DNA fragment is digested with about 2 units of enzyme in about 20 ml of reaction buffer. For the purpose of isolating DNA fragments for plasmid construction. typically 5 to 50 mg of DNA are digested with 20 to 250 units of enzyme in proportionately larger volumes.

Appropriate buffers and substrate amounts for particular restriction enzymes are described in standard laboratory manuals. such as those referenced below. and they are specified by commercial suppliers.

Incubation times of about 1 hour at 37° C. are ordinarily used. but conditions may vary in accordance with standard procedures. the supplier's instructions and the particulars of the reaction. After digestion. reactions may be analyzed. and fragments may be purified by electrophoresis through an agarose or polyacrylamide gel. using well known methods that are routine for those skilled in the art.

GENETIC ELEMENT generally means a polynucleotide comprising a region that encodes a polypeptide or a region that regulates transcription or translation or other processes important to expression of the polypeptide in a host cell. or a polynucleotide comprising both a region that encodes a polypeptide and a region operably linked thereto that regulates expression.

Genetic elements may be comprised within a vector that replicates as an episomal element; that is. as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but. rather. following manipulation such as isolation. cloning and introduction into a host cell in the form of purified DNA or in a vector, among others.

SIMILARITY between two polypeptides is determined by comparing the amino acid sequence and its conserved amino acid substitutes of one polypeptide to the sequence of a second polypeptide. Moreover. also known in the art is "IDENTITY" which means the degree of sequence relatedness between two polypeptide or two polynucleotide sequences as determined by the identity of the match between two strings of such sequences. Both identity and similarity can be readily calculated (Computational Molecular Biology, Lesk. A. M.. ed.. Oxford University Press, New York, 1988; Biocomputing: Informatics and Genome Projects. Smith. D. W.. ed.. Academic Press. New York, 1993; Computer Analysis of Sequence Data. Part I. Griffin. A. M.. and Griffin. H. G.. eds.. Humana Press. New Jersey. 1994; Sequence Analysis in Molecular Biology. von Heinje. G.. Academic Press. 1987; and Sequence Analysis Primer. Gribskov. M. and Devereux. J.. eds.. M Stockton Press. New York. 1991). While there exist a number of methods to measure identity and similarity between two polynucleotide or polypeptide sequences. the terms "identity" and "similarity" are well known to skilled artisans (Sequence Analysis in Molecular Biology. von Heinje. G.. Academic Press. 1987; Sequence Analysis Primer. Gribskov. M. and Devereux. J.. eds.. M Stockton Press. New York. 1991; and Carillo. H.. and Lipman. D.. SIAM J. Applied Math.. 48: 1073 (1988). Methods commonly employed to determine identity or similarity between two sequences include. but are not limited to disclosed in Guide to Huge Computers. Martin J. Bishop. ed.. Academic Press. San Diego. 1994. and Carillo. H.. and Lipman. D.. SIAM J. Applied Math.. 48: 1073 (1988). Preferred methods to determine identity are designed to give the largest match between the two sequences tested. Methods to determine identity and similarity are codified in computer programs. Preferred computer program methods to determine identity and similarity between two sequences include. but are not limited to. GCG program package (Devereux. J.. et al.. Nucleic Acids Research 12(1): 387 (1984)). BLASTP. BLASTN. FASTA (Atschul. S. F. et al.. J. Molec. Biol. 215: 403 (1990)).

ISOLATED means altered "by the hand of man" from its natural state; i.e.. that. if it occurs in nature. it has been changed or removed from its original environment. or both.

For example. a naturally occurring polynucleotide or a polypeptide naturally present in a living animal in its natural state is not "isolated." but the same polynucleotide or polypeptide separated from some or all of the coexisting materials of its natural is "isolated". as the term is employed herein.

As part of or following isolation. such polynucleotides can be joined to other polynucleotides. such as DNAs. for mutagenesis. to form fusion proteins. and for propagation or expression in a host. for instance. The isolated polynucleotides. alone or joined to other polynucleotides such as vectors. can be introduced into host cells. in culture or in whole organisms. Introduced into host cells in culture or in whole organisms. such DNAs still would be isolated. as the term is used herein. because they would not be in their naturally occurring form or environment. Similarly. the polynucleotides and polypeptides may occur in a composition. such as a media formulations. solutions for introduction of polynucleotides or polypeptides. for example. into cells. compositions or solutions for chemical or enzymatic reactions. for instance. which are not naturally occurring compositions. and. therein remain isolated polynucleotides or polypeptides within the meaning of that term as it is employed herein.

LIGATION refers to the process of forming phosphodiester bonds between two or more polynucleotides. which most often are double stranded DNAs. Techniques for ligation are well known to the art and protocols for ligation are described in standard laboratory manuals and references. such as. for instance. Sambrook et al.. MOLECULAR CLONING. A LABORATORY MANUAL. 2nd Ed.; Cold Spring Harbor Laboratory Press. Cold Spring Harbor. N.Y. (1989) and Maniatis et al.. pg. 146. as cited below.

OLIGONUCLEOTIDE(S) refers to relatively short polynucleotides. Often the term refers to single-stranded deoxyribonucleotides. but it can refer as well to single-or double-stranded ribonucleotides. RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors. Meth. Enzymol. 182: 626–646 (1990) and Rattan et al., Protein Synthesis: Posttranslational Modifications and Aging. Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide.

Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with Arginase II polypeptides of the present invention, including not only classic receptors, which are preferred, but also other molecules that specifically bind to or interact with polypeptides of the invention (which also may be referred to as "binding molecules" and "interaction molecules," respectively and as "Arginase II binding molecules" and "Arginase II interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to novel Arginase II polypeptides and polynucleotides, among other things, as described in greater detail below. In particular, the invention relates to polypeptides and polynucleotides of a novel human Arginase II, which is related by amino acid sequence homology to Arginase I, non-type I arginase from Xenopus and agmatinase. The invention relates especially to Arginase II having the nucleotide and amino acid sequences set out in FIG. 2, and to the Arginase II nucleotide and amino acid sequences obtained from a cDNA library in ATCC Deposit No. 75,656, which is herein referred to as "the deposited clone" or as the "cDNA of the deposited clone." It will be appreciated that the nucleotide and amino acid sequences set out in FIG. 2 were obtained by sequencing the cDNA of the deposited clone. Hence, the sequence of the deposited clone is controlling as to any discrepancies between the two.

Polynucleotides

In accordance with one aspect of the present invention, there are provided isolated polynucleotides which encode the Arginase II polypeptide having the deduced amino acid sequence of FIG. 2 or the Arginase II polypeptide encoded by the cDNA in the deposited clone.

Using the information provided herein, such as the polynucleotide sequence set out in FIG. 2, a polynucleotide of the present invention encoding human Arginase II polypeptide may be obtained using standard cloning and screening procedures, such as those for cloning cDNAs using mRNA from cells of a Jurkat cell line library as starting material. Illustrative of the invention, the polynucleotide set out in FIG. 2 was discovered in a cDNA library derived from cells of a human Jurkat cell line library.

Human Arginase II of the invention is structurally related to other proteins of the arginase family, as shown by the results of sequencing the cDNA encoding human Arginase II in the deposited clone. The cDNA sequence thus obtained is set out in FIG. 2. It contains an open reading frame encoding a protein of about 355 amino acid residues with a deduced molecular weight of about 35 kDa. The protein exhibits greatest homology to Arginase I and non-type I arginase from Xenopus, among known proteins. The 355 residues of the Arginase II of FIG. 2 have about 55% identity and about 68% similarity with the amino acid sequence of human type I arginase.

Arginase II is expressed in kidney and to a much greater extent in prostate as determined by northern blot analysis using the Arginase II gene as a probe. Other tissues showed no observable message on northern blots. It is known that express nitric oxide is expressed at extremely high levels in the prostate.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 2 or that of the deposited clone. It also may be a polynucleotide with a different sequence, which, as a result of the redundancy (degeneracy) of the genetic code, encodes the polypeptide of the DNA of FIG. 2 or of the deposited cDNA.

Polynucleotides of the present invention which encode the polypeptide of FIG. 2 or the polypeptide encoded by the deposited cDNA may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the vector pQE-9, among others, many of which are commercially available. As described in Gentz et al., Proc. Natl. Acad. Sci., USA 86: 821–824 (1989), for instance, hexa-histidine provides for convenient purification of the fusion protein. The HA tag corresponds to an epitope derived of influenza hemagglutinin protein, which has been described by Wilson et al., Cell 37: 767 (1984), for instance.

In accordance with the foregoing, the term "polynucleotide encoding a polypeptide" as used herein encompasses polynucleotides which include a sequence encoding a polypeptide of the present invention, particularly the human Arginase II having the amino acid sequence set out in FIG. 2 or the amino acid sequence of the human Arginase II encoded by the cDNA of the deposited clone. The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 or the polypeptide encoded by the cDNA of the deposited clone. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of Arginase II set out in FIG. 2 or the amino acid sequence of Arginase II of the cDNA of the deposited clone; variants, analogs, derivatives and fragments thereof, and fragments of the variants, analogs and derivatives.

Further particularly preferred in this regard are polynucleotides encoding Arginase II variants, analogs, derivatives and fragments, and variants, analogs and derivatives of the fragments, which have the amino acid sequence of the Arginase II polypeptide of FIG. 2 or of the deposit in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the Arginase II. Also especially preferred in this regard are conservative substitutions. Most highly preferred are polypeptides having the amino acid sequence of FIG. 2 or of the deposit, without substitutions.

Further preferred embodiments of the invention are polynucleotides that are at least 70% identical to a polynucleotide encoding the Arginase II polypeptide having the amino acid sequence set out in FIG. 2, or variants, close homologs, derivatives and analogs thereof, as described above, and polynucleotides which are complementary to such polynucleotides. Alternatively, most highly preferred are polynucleotides that comprise a region that is at least 80% identical to a polynucleotide encoding the Arginase II polypeptide of the cDNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the cDNA of FIG. 2 or the cDNA of the deposited clone.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding Arginase II and to isolate cDNA and genomic clones of other genes that have a high sequence similarity to the human Arginase II gene. Such probes generally will comprise at least 15 bases. Preferably, such probes will have at least 30 bases and may have at least 50 bases. Particularly preferred probes will have at least 30 bases and will have 50 bases or less.

For example, the coding region of the Arginase II gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

A deposit containing a human Arginase II cDNA has been deposited with the American Type Culture Collection, as noted above. Also as noted above, the cDNA deposit is referred to herein as "the deposited clone" or as "the cDNA of the deposited clone."

The deposited clone was deposited with the American Type Culture Collection, 12301 Park Lawn Drive, Rockville, Md. 20852, USA, on Jan. 26, 1994, and assigned ATCC Deposit No. 75,656.

The deposited material is a pBluescript SK (−) plasmid library (Stratagene, La Jolla, Calif.) that contains cDNA clones, including those of Arginase II.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. section 112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human Arginase II polypeptide which has the deduced amino acid sequence of FIG. 2 or which has the amino acid sequence encoded by the deposited clone.

The invention also relates to fragments, analogs and derivatives of these polypeptides. The terms "fragment," "derivative" and "analog" when referring to the polypeptide of FIG. 2 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 2 or that encoded by the cDNA in the deposited clone may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of Arginase II set out in FIG. 2, variants, analogs, derivatives and fragments thereof, and variants, analogs and derivatives of the fragments. Alternatively, particularly preferred embodiments of the invention in this regard are polypeptides having the amino acid sequence of the Arginase II of the cDNA in the deposited clone, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the Arginase II polypeptide of FIG. 2 or of the cDNA in the deposited clone, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the Arginase II. Also especially preferred in this regard are conservative substitutions. Most highly preferred are polypeptides having the amino acid sequence of FIG. 2 or the deposited clone without substitutions.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of Arginase II, most particularly fragments of the Arginase II having the amino acid set out in FIG. 2, or having the amino acid sequence of the Arginase II of the deposited clone, and fragments of variants and derivatives of the Arginase II of FIG. 2 or of the deposited clone.

In this regard a fragment is a polypeptide having an amino acid sequence that entirely is the same as part but not all of the amino acid sequence of the aforementioned Arginase II polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a Arginase II polypeptide of the present comprised within a precursor polypeptide designed for expression in a host and having heterologous pre and pro-polypeptide regions fused to the amino terminus of the Arginase II fragment and an additional region fused to the carboxyl terminus of the fragment. Therefore, fragments in one aspect of the meaning intended herein, refers to the portion or portions of a fusion polypeptide or fusion protein derived from Arginase II.

As representative examples of polypeptide fragments of the invention, there may be mentioned those which have from about 8 to about 16 amino acids which include the regions of high cross-species homology and polypeptide fragments of the invention which have from about 20 to 50 amino acids which include the regions of lowest homolgy between type I arginase and the sequence reported in FIG. 2.

In this context about includes the particularly recited range and ranges larger or smaller by several, a few, 5, 4, 3, 2 or 1 amino acid at either extreme or at both extremes. For instance, about 65–90 amino acids in this context means a polypeptide fragment of 65 plus or minus several, a few, 5, 4, 3, 2 or 1 amino acids to 90 plus or minus several a few, 5, 4, 3, 2 or 1 amino acid residues, i.e., ranges as broad as 65 minus several amino acids to 90 plus several amino acids to as narrow as 65 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 8 to about 50 amino acids to include six areas of high cross-species homology which most likely contribute to the active site of the enzyme and three areas of low cross species homology which may be of greatest diagnostic significance.

Among especially preferred fragments of the invention are truncation mutants of Arginase II. Truncation mutants include Arginase II polypeptides having the amino acid sequence of FIG. 2, or of the deposited clone, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of Arginase II. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of Arginase II.

Certain preferred regions in these regards are set out in FIG. 2, and include, but are not limited to, regions of the aforementioned types identified by analysis of the amino acid sequence set out in FIG. 2. As set out in FIG. 2, such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of Arginase II that combine several structural features, such as several of the features set out above. In this regard, the regions defined by the residues about amino acids 116–123, amino acids 141–153, amino acids 156–168, amino acids 193–206, amino acids 249–261, amino acids 265–286, amino acids 96–115, amino acids 213–248, and amino acids 306–356 of FIG. 2, which are regions of either high cross-species homology, thus potentially involved in the active site of the enzyme, or regions of low-cross species homology which may increase their usefulness in generating arginase II specific antibodies or use for arginase II specific DNA based diagnostics. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of Arginase II. Most highly preferred in this regard are fragments that have a chemical, biological or other activity of Arginase II, including those with a similar activity or an improved activity, or with a decreased undesirable activity. Highly preferred in this regard are fragments that contain regions that are homologs in sequence, or in position, or in both sequence and to active regions of related polypeptides, such as, for example, the related polypeptides set out in FIG. 4, which include arginases. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, such as, for example SEQ ID NO:3–15, for amplifying polynucleotides that encode the fragments. In these regards, preferred polynucleotides are those that correspondent to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the E. coli lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing E. coli and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH 16a, pNH 18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT I and pSG available from Stratagene; and pSVK3, pBPV, pMSG and pSVL available from Pharmacia. These vectors are listed solely by way of illustration of the many vectors commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. Coli and the trp1 gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include Escherischia coli, Bacillus subtilis and Salmonella typhimurium. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C1 27, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The Arginase II polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

FURTHER ILLUSTRATIVE ASPECTS AND PREFERRED EMBODIMENTS OF THE INVENTION

Arginase II polynucleotides and polypeptides may be used in accordance with the present invention for a variety of applications, particularly those that make use of the chemical and biological properties Arginase II. Among these are applications in diagnosis and treatment of urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage. Additional applications relate to diagnosis and to treatment of disorders of cells, tissues and organisms.

Methods of using Arginase II are also provided to control nitric oxide formation in an individual having a need to control such formation, and to treat systemic hypotension caused by sepsis or cytokines using Arginase II alone or in combination with an alpha sub-1 adrenergic agonist.

A method for using Arginase II polypeptides to prepare or synthesize of L-ornithine salts is provided. Such salts are useful in chemical reactions, industrial and pharmaceutical applications. Skilled artisans will readily be able to produce useful quantities of such salts using large scale cell culture or fermentation with cells comprising the Arginase II gene.

These aspects of the invention are illustrated further by the following discussion.

Polynucleotide Assays

This invention is also related to the use of the Arginase II polynucleotides to detect complementary polynucleotides such as, for example, as a diagnostic reagent. Detection of a mutated form of Arginase II associated with a dysfunction will provide a diagnostic tool that can add or define a diagnosis of a disease or susceptibility to a disease which results from under-expression over-expression or altered expression of Arginase II, such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage.

Host organisms carrying mutations in the human Arginase II gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature, 324: 163–166 (1986)). RNA or cDNA may also be used in the same ways. As an example, PCR primers complementary to the nucleic acid encoding Arginase II can be used to identify and analyze Arginase II expression and mutations. For example, deletions and insertions can be detected by a change in size of the amplified product in comparison to the normal genotype. Point mutations can be identified by hybridizing amplified DNA to radiolabeled Arginase II RNA or alternatively, radiolabeled Arginase II antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags. In situ nucleic acid amplification methods, such as, for example, PCR reactions can also be carried out using biopsied tissues and cell samples using well known methods.

One embodiment of the invention is the use of polynucleotides of the invention to detect Arginase II gene expression in prostate cells as a marker for a disease or susceptibility to a disease which results from under-expression overexpression or altered expression of Arginase II, such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage, prostate disease or prostate damage. A preferred embodiment of the invention is using polynucleotides of the invention to detect cells which are expressing an aberrant or variant Arginase II gene or expressing Arginase II gene in an inappropriate tissue to diagnose and prognose disease. Another preferred embodiments of such methods is to detect cells circulating in the blood which express an Arginase II gene, particularly to prognose or stage prostate disease. Circulating cells of the prostate or kidney expressing an Arginase II gene are useful to diagnose or prognose late prostate or kidney cancer respectively, particularly, with respect to prostate cancer, stages C or D, as such stages are known in the art (see, for example, Dugan J. A., et al. JAMA 275: 288 (1996)). A more preferred embodiment of the invention provides that polynucleotides of the invention may be used to detect and quantitate levels of Arginase II expression in cells. As compared with normal Arginase II expression in a cell, detection of higher levels of expression is useful for prognosis of the stage of a disease, particularly for cancer, especially kidney and prostate cancer. Detection of Arginase II expression in cells of the prostate or kidney with no detectable concomitant expression in cells circulating in the blood is useful to diagnose early stage prostate or kidney cancer respectively, particularly, with respect to prostate cancer, stages A or B, as such stages are known in the art.

Other preferred embodiments include a method for the diagnosis of a disorder arising from Arginase II deficiency in a host organism having or suspected of having a defect in the nitric oxide pathway and the urea cycle using Arginase II polynucleotides, polypeptides and antibodies, including but not limited to fragments of either. Arginase II polynucleotides, polypeptides, and antibodies, can be used in a method to monitor progression or therapy of disorders with hypotension as a clinical sign, to monitor progression of or therapy of disorders of the immune or nervous systems associated with or caused by nitric oxide regulation, to monitor activation state of macrophage, or to monitor mitochondrial activity as a function of the transportation of arginase II into the mitochondria.

RT-PCR is a well known method (Kawasaki E. S., et al., Proc Natl Acad Sci. USA 85: 5698 (1988)). Polynucleotides of the invention are particularly useful for RT-PCR for detection of Arginase II gene expression. Polynucleotides of the invention may be used as primers to mediate the reverse transcription reaction of RT-PCR, and may also be used as primers for the PCR reaction.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S 1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA. In situ hybridization reactions can also be carried out using biopsied tissues and cell samples using well known methods.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a Arginase II gene. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide Assays

The present invention also relates to a diagnostic assays such as quantitative and diagnostic assays for detecting levels of Arginase II protein in cells and tissues, including determination of normal and abnormal levels. Thus, for instance, a diagnostic assay in accordance with the invention for detecting over-expression of Arginase II protein compared to normal control tissue samples may be used to detect the presence of urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage, for example. Assay techniques that can be used to determine levels of a protein, such as an Arginase II protein of the present invention, in a sample derived from a host are well-known to those of skill in the art. Such assay methods include radioimmunoassays, competitive-binding assays, Western Blot analysis and ELISA assays. Preferred samples to be assayed using these assays, include, but are not limited to cells, tissues and bodily fluids. Among these ELISAs frequently are preferred. An ELISA assay initially comprises preparing an antibody specific to Arginase II, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample, such as, for example, bodily fluid, is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any Arginase II proteins attached to the polystyrene dish. Unbound monoclonal antibody is washed out with buffer. The reporter antibody linked to horseradish peroxidase is placed in the dish resulting in binding of the reporter antibody to any monoclonal antibody bound to Arginase II. Unattached reporter antibody is then washed out. Reagents for peroxidase activity, including a colorimetric substrate are then added to the dish. Immobilized peroxidase, linked to Arginase II through the primary and secondary antibodies, produces a colored reaction product. The amount of color developed in a given time period indicates the amount of Arginase II protein present in the sample. Quantitative results typically are obtained by reference to a standard curve.

A competition assay may be employed wherein antibodies specific to Arginase II attached to a solid support and labeled Arginase II and a sample derived from the host are passed over the solid support and the amount of label detected attached to the solid support can be correlated to a quantity of Arginase II in the sample.

One embodiment of the invention is the use of polypeptide assays of the invention to detect Arginase II gene expression in prostate cells as a marker for a disease or susceptibility to a disease which results from under-expression over-expression or altered expression of Arginase II, such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage, prostate disease or prostate damage. A preferred assay embodiment of the invention is to detect cells which are expressing an aberrant or variant Arginase II gene or expressing Arginase II gene in an inappropriate tissue to diagnose and prognose disease. Another preferred embodiment of such methods is to detect cells circulating in the blood which express an Arginase II gene, particularly to prognose or stage prostate disease. Circulating cells of the prostate or kidney expressing an Arginase II gene are useful to diagnose or prognose late prostate or kidney cancer respectively, particularly, with respect to prostate cancer, stages C or D, as such stages are known in the art. A more preferred embodiment of the invention provides that assays of the invention may be used to detect and quantitate levels of Arginase II expression in cells. As compared with normal Arginase II expression in a cell, detection of higher levels of expression is useful for prognosis of the stage of a disease, particularly for cancer, especially kidney and prostate cancer. Detection of Arginase II expression in cells of the prostate or kidney with no detectable concomitant expression in cells circulating in the blood is useful to diagnose early stage prostate or kidney cancer respectively, particularly, with respect to prostate cancer, stages A or B, as such stages are known in the art.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Thus, among others, such antibodies can be used to treat such as, for example, urea cycle diseases, hypertension, hypotension, episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage.

The methods of the invention to detect and/or quantitate Arginase II polynucleotide sequence, Arginase II expression levels and gene expression products, particularly the immunological and immunohistochemical methods and methods using oligonucleotides, can be used with bodily tissues and fluids from individuals. Preferred bodily tissues and fluids useful with the methods of the invention include, but are not limited to, cells and tissues of the liver, kidney, brain, gastrointestinal tract, mammary gland, particularly while lactating, and blood, particularly red blood cells, and activated macrophages. Preferred bodily samples useful with the immunohistochemical methods of the invention include, but are not limited to, tissues and cells.

Arginase II Binding Molecules and Assays

This invention also provides a method for identification of molecules, such as receptor molecules, that bind Arginase II. Genes encoding proteins that bind Arginase II, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to Arginase II, a cDNA library is created from this RNA, the library is divided into pools and the pools are transfected individually into cells that are not responsive to Arginase II. The transfected cells then are exposed to labeled Arginase II. (Arginase II can be labeled by a variety of well-known techniques including standard methods of radio-iodination or inclusion of a recognition site for a site-specific protein kinase.) Following exposure, the cells are fixed and binding of Arginase II is determined. These procedures conveniently are carried out on glass slides.

Pools are identified of cDNA that produced Arginase II-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess Arginase II binding capacity of Arginase II binding molecules, such as receptor molecules, in cells or in cell-free preparations.

Agonists and Antagonists—Assays and Molecules

The invention also provides a method of screening compounds to identify those which enhance or block the action of Arginase II on cells, such as its interaction with Arginase II-binding molecules such as receptor molecules. An agonist is a compound which increases the natural biological functions of Arginase II, while antagonists decrease or eliminate such functions.

For example, a cellular compartment, such as a membrane or a preparation thereof, such as a membrane-preparation, may be prepared from a cell that expresses a molecule that binds Arginase II, such as a molecule of a signaling or regulatory pathway modulated by Arginase II. The preparation is incubated with labeled Arginase II in the absence or the presence of a candidate molecule which may be a Arginase II agonist or antagonist. The ability of the candidate molecule to bind the binding molecule is reflected in decreased binding of the labeled ligand. Molecules which bind gratuitously, i.e., without inducing the effects of Arginase II on binding the Arginase II binding molecule, are most likely to be good antagonists. Molecules that bind well and elicit effects that are the same as or closely related to Arginase I, for example, are agonists.

Arginase II-like effects of potential agonists and antagonists may by measured, for instance, by determining activity of a second messenger system following interaction of the candidate molecule with a cell or appropriate cell preparation, and comparing the effect with that of Arginase II or molecules that elicit the same effects as Arginase II. Second messenger systems that may be useful in this regard include but are not limited to AMP guanylate cyclase, ion channel or phosphoinositide hydrolysis second messenger systems.

Another example of an assay for Arginase II antagonists is a competitive assay that combines Arginase II and a potential antagonist with membrane-bound Arginase II receptor molecules or recombinant Arginase II receptor molecules under appropriate conditions for a competitive inhibition assay. Arginase II can be labeled, such as by radioactivity, such that the number of Arginase II molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing Arginase II-induced activities, thereby preventing the action of Arginase II by excluding Arginase II from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Arginase II. The antisense RNA oligonucleotide hybridizes to the mRNA in vivo and blocks translation of the mRNA molecule into Arginase II polypeptide. The oligonucleotides described above can also be delivered to cells such that the antisense RNA or DNA may be expressed in vivo to inhibit production of Arginase II.

The antagonists may be employed in a composition with a pharmaceutically acceptable carrier, e.g., as hereinafter described.

The antagonists may be employed for instance to treat an individual having or suspected of having a disease associated with or caused by a defect in the Arginase II gene or Arginase II gene expression, such as, for example, urea cycle diseases, hypertension, hypotension episodic hyperammonemia, defects in biosynthesis of proline, glutamate, nitric oxide and ornithine, as well as hyperargininemia and its related spasticity, growth retardation, and progressive mental impairment, and prostate disease, particularly prostate cancer, prostatitis and benign prostatic hyperplasia or hypertrophy, and also prostate damage, kidney disease, and kidney damage.

Antagonist and agonists of the invention, including but not limited to antibodies, can be used in method to deplete systemic arginine levels in an individual having a need for a depletion of such levels.

Arginase II is involved in the nitric oxide pathway. Nitric oxide is a very important regulatory molecule and arginase regulates nitric oxide synthesis through the production of ornithine from arginine. This regulation is a key to the involvement of arginase, and as provided herein Arginase II, in hypotension, macrophage killing and immune function, and in the nervous system.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 mg/kg body weight. In most cases they will be administered in an amount not in excess of about 8 mg/kg body weight per day. Preferably, in most cases, dose is from about 10 mg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The Arginase II polynucleotides, polypeptides, agonists and antagonists that are polypeptides may be employed in accordance with the present invention by expression of such polypeptides in vivo, in treatment modalities often referred to as "gene therapy."

A preferred embodiment of the invention is treatment of disease associated or caused by defects in nitric oxide biosynthesis using Arginase II in gene therapy. Arginase II may also be used in gene therapy to treat defects of type I arginase, particularly those defects associated with of which cause nitric oxide biosynthesis disorders. Also provided is a method of using gene therapy to treat immunologic and/or neurologic disorders associated with or caused by nitric oxide dysfunction, particularly those which are a result of Arginase II deficiency.

A further preferred embodiment of the invention is a method of using gene therapy to treat disorders resulting in hyperargininemia, to include but not be limited to defects in arginase Type I and Type II genes.

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and ∝-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the ∝-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP⁺E-86, GP⁺envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and CaPO₄ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 mg of DNA.

Example 1
Cloning of the Human Arginase II cDNA

The cDNA sequence of Arginase I was used as a probe sequence for a computer search (Kerlavage et al., In: *Proceedings of the 26th Hawaii International Symposium on System Sciences* 585–594 (1993)) of a cDNA database comprising EST sequences (the "research database") made by random sequenceing of human cDNA libraries with an ABI 373 sequencer using well known methods (see, for example, Adams, et al. *Nature* 368: 474 (1994)). The sequences were stored in an electronically searchable database. This database comprises sequences of the deposited clone. A number of ESTs were identified that had 100% homology to Arginase 1. Another subset of ESTs were identified which had between 50% and 60% homology to Arginase I. Upon closer examination most of these ESTs had regions which were approximately 70% homologous at the nucleic acid level to Arginase I but other regions were significantly different. Utilizing the University of Wisconsin GCG programs these ESTs (FIG. 1(B)) were compiled into a contiguous DNA sequence (FIG. 1(A)). By utilizing flanking non-homologous sequences as new probe sequences, the contig was expanded both 5' and 3' until the research database was exhausted of overlapping clones. The sequence of all overlapping clones was used to generate a consensus sequence of 1075 bases. PCR primers were designed to the extreme 3' and 5' ends of the consensus sequence (FIG. 3 (SEQ ID NO:3–15)). Skilled artisans can readily obtain such amplification using the primers of the invention, including, for example, those in FIG. 3 (SEQ ID NO:3–15). A Jurkat cell line cDNA library was PCR amplified with the flanking primers resulting in a single, clear band when the amplicon was visualized on an agarose gel after ethidium bromide staining. The resulting amplicon was cloned into the TA cloning vector (Clontech Inc.) and sequenced in both directions. The final sequence was compared to the consensus derived from the research database search and is presented in FIG. 2 along with a computer generated translation of 355 amino acids (SEQ ID NO:2).

Comparison of the nucleic acid and protein translation of the proposed Arginase II clone to that of Arginase I identified six highly conserved regions between the two molecules (FIG. 5). These are the same six regions of cross-species homology identified in Arginase I from virtually all species studied. The nucleic acid homology in the conserved regions is approximately 70% while in the adjacent non-conserved regions, homology drops to below 40%. Similarly, when the amino acid sequence of the putative Arginase II protein was compared to the know sequence of Arginase I, the six regions of cross-species homology were conserved between Arginase I and Arginase II (FIG. 5). Only six amino acid residues out of the 79 residues included in the conserved region are different between Arginase I and Arginase II giving a homology within the conserved region of 92%. Outside of the conserved regions amino acid homology averages around 42%.

The sequence of known arginase molecules was used to generate an phylogenetic tree using GCG software well known in the art. This analysis demonstrated that the human Arginase II sequence is more closely related to "non-type I" arginase from Xenopus than it is related to human Arginase I.

The full length Arginase II clone identified from a Jurkat cDNA library may be subcloned into the expression vector pTRC99A for arginase expression studies.

The DNA sequence encoding human Arginase II in the deposited polynucleotide can be amplified using PCR oligonucleotide primers specific to the amino acid carboxyl terminal sequence of the human Arginase II protein and to the end of the contig (FIG. 3 (SEQ ID NO:3–15)). Additional nucleotides containing restriction sites to facilitate cloning were added to the 5' and 3' sequences respectively. No additional nucleotides were added. It was cloned into a TA cloning vector.

The 5' oligonucleotide primer had the sequence 5'-ATGT CCCTAAGGGGCAGCCTCTCGCGTC-3' (SEQ ID NO:3) which encodes a start AUG, followed by 25 nucleotides of the human Arginase II coding sequence set out in FIG. 2 beginning with the first base of the AUG start codon.

The 3' primer had the sequence 5'-TAA ATTCTCACACGTGCTTGATTTTCTG-3' (SEQ ID NO:4) complementary to the last 28 nucleotides of the Arginase II coding sequence set out in FIG. 2, including the stop codon.

The restrictions sites were generated using primers 5F and 5R in FIG. 3 and were convenient to restriction enzyme sites in the bacterial expression vectors pTRC99A, which were used for bacterial expression in these examples (Pharmacia). pTRC99A encodes ampicillin antibiotic resistance ("Ampr") and contains a bacterial origin of replication ("ori"), an IPTG inducible promoter, a ribosome binding site ("RBS") and restriction enzyme sites.

The amplified human Arginase II DNA and the vector pTRC99A both were digested with EcoRI and PstI and the digested DNAs then were ligated together. Insertion of the Arginase II DNA into the pTRC99A restricted vector placed the Arginase II coding region downstream of and operably linked to the vector's IPTG-inducible promoter and in-frame with an initiating AUG appropriately positioned for translation of Arginase II.

The ligation mixture was transformed into competent E. coli cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989).

E. coli strain M15/rep4, containing multiple copies of the plasmid pREP4, which expresses lac repressor and confers kanamycin resistance ("Kanr"), is used in carrying out the illustrative example described here. This strain, which is only one of many that are suitable for expressing Arginase II, is available commercially from Qiagen.

Transformants are identified by their ability to grow on LB plates in the presence of ampicillin. Plasmid DNA is isolated from resistant colonies and the identity of the cloned DNA and is confirmed by restriction analysis.

Clones containing the desired constructs are grown overnight ("O/N") in liquid culture in LB media supplemented with both ampicillin (100 ug/ml) and kanamycin (25 ug/ml).

The O/N culture is used to inoculate a large culture, at a dilution of approximately 1:100 to 1:250. The cells are grown to an optical density at 600 nm ("OD") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2× PBS at a concentration of 95 micrograms per ml.

Analysis of the preparation by standard methods of polyacrylamide gel electrophoresis is expected to reveal that the preparation contains monomeric Arginase II.

Example 2
Analysis of Human Arginase II cDNA

Utilizing the Arginase I cDNA sequence, 21 overlapping clones were identified in the research database which have sequence homology to, but were distinct from, Arginase I. These clones were used to generate a full length cDNA of 1075 bases, which, upon examination, proved to be a previously novel arginase gene, Arginase II (FIG. 2 (SEQ ID NO:1–2)). The pattern of expression of Arginase II, as determined by antibody studies, has striking similarity to the origin of the libraries that contained positive clones. The clones listed in FIG. 1 are derived from white cell lineage, the gastrointestinal tract and brain. However, clones from the kidney and lactating mammary gland, two tissues known to express Arginase II may be present. In addition, a major source of clones from the research database is from prostate tissue library sequence. These include normal and cancerous prostatic tissues and tissue from patients with benign hyperplasia of the prostate.

The sequence of the clone recovered from a Jurkat cDNA library was identical to the consensus derived by the overlapping clones from the research database verifying the correct sequence of the gene. Comparison of this sequence to the known sequence of arginase I identifies six conserved regions in Arginase II. The homology within these conserved regions is approximately 70%. Divergence between the sequences is limited to the wobble position in almost every one of the codons in the conserved region, resulting in 92% conservation at the amino acid level. Considering the low level of homology between the two types of arginase outside of the conserved region, maintenance of the bases essential to conservation of the amino acid sequence in these regions, gives some indication of how important these residues are to enzymatic activity. In spite of evolutionary pressure for the two sequences to diverge, selection, based on function has preserved the conserved regions. While Arginase II contains all of the conserved regions present in Arginase I, the phylogenetic tree demonstrated that human Arginase II is more closely related to the non-hepatic form of arginase from Xenopus than to human Arginase I.

Example 3
Cloning and Expression of Human Arginase II in a Baculovirus Expression System The cDNA sequence encoding the full length human Arginase II protein, in the deposited clone can be amplified using PCR oligonucleotide primers corresponding to the 5' and 3' sequences of the gene using methods well known in the art. Inserted into an expression vector, as described below, the 5' end of the amplified fragment encoding human Arginase II may provide an efficient signal peptide. An efficient signal for initiation of translation in eukaryotic cells, as described by Kozak, M., J. Mol. Biol. 196: 947–950 (1987) is appropriately located in the vector portion of the construct.

An amplified fragment may be isolated from a 1% agarose gel using a commercially available kit ("Geneclean," BIO 101 Inc., La Jolla, Calif.). The fragment then is digested with the appropriate restriction endonucleases and again is purified on a 1% agarose gel. This fragment is designated herein F2.

Expression vectors known in the art will be useful to express the Arginase II protein in a baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). A preferred expression vector contains the strong polyhedrin promoter of the Autographa californica nuclear polyhedrosis virus (AcMNPV) followed by convenient restriction sites. Preferably, the signal peptide of AcMNPV gp67, including the N-terminal methionine, is located just upstream of a BamH I site. Preferably, the polyadenylation site of the simian virus 40 ("SV40") is used for efficient polyadenylation. Preferably, for an easy selection of recombinant virus the beta-galactosidase gene from *E. coli* is inserted in the same orientation as the polyhedrin promoter and is followed by the polyadenylation signal of the polyhedrin gene. Preferably, the polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with appropriate restriction enzymes and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase.*E. coli* HB101 cells are transformed with ligation mix and spread on culture plates. Bacteria are identified that contain the plasmid with the human Arginase II gene by digesting DNA from individual colonies using restriction enzymes appropriate to remove the inserted sequence using known methods and then analyzing the digestion product by gel electrophoresis. The sequence of the cloned fragment is confirmed by DNA sequencing. This plasmid is designated herein pBacArginase II. 5 mg of the plasmid pBacArginase II is co-transfected with 1.0 mg of a commercially available linearized baculovirus DNA (BaculoGold baculovirus DNA, Pharmingen, San Diego, Calif.), using the lipofection method described by Felgner et al., Proc. Natl. Acad. Sci. USA 84: 7413–7417 (1987). 1 mg of BaculoGold virus DNA and 5 mg of the plasmid pBacArginase II are mixed in a sterile well of a microtiter plate containing 50 ml of serum free Grace's medium (Life Technologies Inc., Gaithersburg, Md.). Afterwards 10 ml Lipofectin plus 90 ml Grace's medium are added, mixed and incubated for 15 minutes at room temperature. Then the transfection mixture is added drop-wise to Sf9 insect cells (ATCC CRL 1711) seeded in a 35 mm tissue culture plate with I ml Grace's medium without serum. The plate is rocked back and forth to mix the newly added solution. The plate is then incubated for 5 hours at 27° C. After 5 hours the transfection solution is removed from the plate and I ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with Blue Gal (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 ml of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted Arginase II is identified by DNA analysis including restriction mapping and sequencing. This is designated herein as V-Arginase II.

Sf9 cells are grown in Grace's medium supplemented with 10% heat-inactivated FBS. The cells are infected with the recombinant baculovirus V-Arginase II at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 mCi of $^{35}$S-methionine and 5 mCi 35S cysteine (available from Amersham) are added. The cells are further incubated for 16 hours and then they are harvested by centrifugation, lysed and the labeled proteins are visualized by SDS-PAGE and autoradiography.

Example 4
Expression of Arginase II in COS Cells

The expression plasmid, Arginase II HA, is made by cloning a cDNA encoding Arginase II into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire Arginase II precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows. The Arginase II cDNA of the deposit clone is amplified using primers that contained convenient restriction sites, much as described above regarding the construction of expression vectors for expression of Arginase II in *E. Coli* and *S. furgiperda*.

To facilitate detection, purification and characterization of the expressed Arginase II, one of the primers contains a heamaglutinin tag ("HA tag") as described above.

PCR amplified DNA fragments and the vector, pcDNAI/Amp, are digested with and then ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the Arginase II-encoding fragment.

For expression of recombinant Arginase II, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989).

Cells are incubated under conditions for expression of Arginase II by the vector.

Expression of the Arginase II HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 5
Tissue Distribution of Arginase II Expression

Northern blot analysis is carried out to examine the levels of expression of Arginase II in human tissues, using methods described by, among others, Sambrook et al, cited above. Premade Clontech were used for northern blots. Total cellular RNA samples are isolated with RNAzol B system (Biotecx Laboratories, Inc. 6023 South Loop East, Houston, Tex. 77033).

About 10mg of Total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes Arginase II, the antisense strand of the coding region of the cDNA insert in the deposited clone is labeled to a high specific activity. The cDNA is labeled by primer extension, using the Prime-It kit, available from Stratagene. The reaction is carried out using 50 ng of the cDNA, following the standard reaction protocol as recommended by the supplier. The labeled polynucleotide is purified away from other labeled reaction components by column chromatography using a Select-G-50 column, obtained from 5-Prime-3-Prime, Inc. of 5603 Arapahoe Road, Boulder, Colo. 80303.

The labeled probe is hybridized to the filter, at a concentration of 1,000,000 cpm/ml, in a small volume of 7% SDS, 0.5M NaPO4, pH 7.4 at 65° C., overnight.

Thereafter the probe solution is drained and the filter is washed twice at room temperature and twice at 60° C. with 0.5× SSC, 0.1% SDS. The filter then is dried and exposed to film at −70° C. overnight with an intensifying screen.

Autoradiography shows that mRNA for Arginase II is abundant in prostate and to a lesser extent (approximately 5–10-fold less) in kidney.

Example 6
Gene Therapeutic Expression of Human Arginase II

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

Arginase II cDNA capable of expressing active Arginase II, is isolated. The ends of the fragment are modified, if necessary, for cloning into the vector. For instance, 5' overhanging may be treated with DNA polymerase to create blunt ends. 3' overhanging ends may be removed using S 1 nuclease. Linkers may be ligated to blunt ends with T4 DNA ligase.

Equal quantities of the Moloney murine leukemia virus linear backbone and the Arginase II fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the Arginase II gene is introduced into the packaging cells by standard techniques. Infectious viral particles containing the Arginase II gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce Arginase II product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1303 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
GCGGANCTCT  GCCTTGGAGA  TTCTCAGTGC  TGCGGATCAT  GTCCCTAAGG  GGCAGCCTCT      60

CGCGTCTCCT  CCAGACGCGA  GTGCATTCCA  TCCTGAAGAA  ATCCGTCCAC  TCCGTGGCTG     120

TGATAGGAGC  CCCGTTCTCA  CAAGGGCAGA  AAAGAAAGG   AGTGGAGCAT  GGTCCCGCTG     180

CCATAAGAGA  AGCTGGCTTG  ATGAAAAGGC  TCTCCAGTTT  GGGCTGCCAC  CTAAAAGACT     240

TTGGAGATTT  GAGTTTTACT  CCAGTCCCCA  AAGATGATCT  CTACAACAAC  CTGATAGTGA     300

ATCCACGCTC  AGTGGGTCTT  GCCAACCAGG  AACTGGCTGA  GGTGGTTAGC  AGAGCTGTGT     360

CAGATGGCTA  CAGCTGTGTC  ACACTGGGAG  GAGACCACAG  CCTGGCAATC  GGTACCATTA     420

GTGGCCATGC  CCGACACTGC  CCAGACCTTT  GTGTTGTCTG  GGTTGATGCC  CATGCTGACA     480

TCAACACACC  CCTTACCACT  TCATCAGGAA  ATCTCCATGG  ACAGCCAGTT  TCATTTCTCC     540

TCAGAGAACT  ACAGGATAAG  GTACCACAAC  TCCCAGGATT  TTCCTGGATC  AAACCTTGTA     600

TCTCTTCTGC  AAGTATTGTG  TATATTGGTC  TGAGAGACGT  GGACCCTCCT  GAACATTTTA     660

TTTTAAAAGG  AACTATGGAT  ATCCAGTATT  TTTTCCATGG  AGGAGATATT  GGATCGAACT     720

TGGTATCCAG  GAAGGTCATG  GGAACGGAAC  ATTTGATCTG  GCTGATTGGC  AAGAGACAAA     780
```

-continued

```
GACCAATCCA TTTGAGTTTT GATATTGATG CATTTGACCC TACACTGGCT CCAGCCACAG      840
GAACTCCTGT TGTCGGGGGA CTAACCTATC GAGAAGGCAT GTATATTGCT GAGGAAATAC      900
ACAATACAGG GTTGCTATCA GCACTGGATC TTGTTGAAGT CAATCCTCAG TTGGCCACCT      960
CAGAGGAAGA GGCGAAGACT ACAGCTAACC TGGCAGTAGA TGTGATTGCT TCAAGCTTTG     1020
GTCAGACAAG AGAAGGAGGG CATATTGTCT ATGACCAACT TCCTACTCCC AGTTCACCAG     1080
ATGAATCAGA AAATCAAGCA CGTGTGAGAA TTTAGGAGAC ACTGTGCACT GACATGTTTC     1140
ACAACAGGCA TTCCAGAATT ATGAGGCATT GAGGGGATAG ATGAATACTT AAATGGTTGT     1200
TCTGGGTCAA TACTGCCTTA ATGGGGACAT TTACACATTC TCACATTGTA AAGTTTTCCC     1260
CCCTATTTGG NGACCATNAT TACTGTAAAT GGNNTTTGGG TTT                      1303
```

( 2 ) INFORMATION FOR SEQ ID NO:2:

( i ) SEQUENCE CHARACTERISTICS:
        ( A ) LENGTH: 358 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Met Ser Leu Arg Gly Ser Leu Ser Arg Leu Leu Gln Thr Arg Val His
 1               5                  10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
        35                  40                  45

Ile Arg Glu Ala Gly Leu Met Lys Arg Leu Ser Ser Leu Gly Cys His
    50                  55                  60

Leu Lys Asp Phe Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
        115                 120                 125

Gly His Ala Arg His Cys Pro Asp Leu Cys Val Val Trp Val Asp Ala
    130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Pro Glu His Phe Ile
        195                 200                 205

Leu Lys Gly Thr Met Asp Ile Gln Tyr Phe Phe His Gly Gly Asp Ile
    210                 215                 220
```

| Gly | Ser | Asn | Leu | Val | Ser | Arg | Lys | Val | Met | Gly | Thr | Glu | His | Leu | Ile |
|-----|-----|-----|-----|-----|-----|-----|-----|-----|-----|-----|-----|-----|-----|-----|-----|
| 225 |     |     |     |     | 230 |     |     |     | 235 |     |     |     |     |     | 240 |
| Trp | Leu | Ile | Gly | Lys | Arg | Gln | Arg | Pro | Ile | His | Leu | Ser | Phe | Asp | Ile |
|     |     |     |     | 245 |     |     |     |     | 250 |     |     |     |     | 255 |     |
| Asp | Ala | Phe | Asp | Pro | Thr | Leu | Ala | Pro | Ala | Thr | Gly | Thr | Pro | Val | Val |
|     |     |     | 260 |     |     |     |     | 265 |     |     |     |     | 270 |     |     |
| Gly | Gly | Leu | Thr | Tyr | Arg | Glu | Gly | Met | Tyr | Ile | Ala | Glu | Glu | Ile | His |
|     |     | 275 |     |     |     |     | 280 |     |     |     |     | 285 |     |     |     |
| Asn | Thr | Gly | Leu | Leu | Ser | Ala | Leu | Asp | Leu | Val | Glu | Val | Asn | Pro | Gln |
|     | 290 |     |     |     |     | 295 |     |     |     |     | 300 |     |     |     |     |
| Leu | Ala | Thr | Ser | Glu | Glu | Glu | Ala | Lys | Thr | Thr | Ala | Asn | Leu | Ala | Val |
| 305 |     |     |     |     | 310 |     |     |     |     | 315 |     |     |     |     | 320 |
| Asp | Val | Ile | Ala | Ser | Ser | Phe | Gly | Gln | Thr | Arg | Glu | Gly | Gly | His | Ile |
|     |     |     |     | 325 |     |     |     |     | 330 |     |     |     |     | 335 |     |
| Val | Tyr | Asp | Gln | Leu | Pro | Thr | Pro | Ser | Ser | Pro | Asp | Glu | Ser | Glu | Asn |
|     |     |     | 340 |     |     |     |     | 345 |     |     |     |     | 350 |     |     |
| Gln | Ala | Arg | Val | Arg | Ile |
|     |     | 355 |     |     |     |

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

ATGTCCCTAA GGGGCAGCCT CTCGCGTC    28

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

TAAATTCTCA CACGTGCTTG ATTTTCTG    28

(2) INFORMATION FOR SEQ ID NO:5:

(i) SEQUENCE CHARACTERISTICS:
        (A) LENGTH: 30 base pairs
        (B) TYPE: nucleic acid ( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

CTCTGCCTTG GAGATTCTCA GTGCTGCGGA 30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

ATTGTCTCCT AAATTCTCAC ACGTGCTTGA 30

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

GAGGTGGTTA GCAGAGCTGT GTCAGAT 27

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

CAACAGGAGT TCCTGTGGCT GG                                                        22

( 2 ) INFORMATION FOR SEQ ID NO:9:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

GCTGATTGGC AAGAGACAAA GACCAATCCA                                                30

( 2 ) INFORMATION FOR SEQ ID NO:10:

( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

GGGCATGGCC ACTAATGGTA CCGATTGCC                                                 29

( 2 ) INFORMATION FOR SEQ ID NO:11:

( i ) SEQUENCE CHARACTERISTICS:
                ( A ) LENGTH: 47 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:11:

GATTGCCTTA TGGAATTCAT GTCCCCTAAG GGGCAGCCTC TCGCGTC                             47

( 2 ) INFORMATION FOR SEQ ID NO:12:

( i ) SEQUENCE CHARACTERISTICS:
                ( A ) LENGTH: 43 base pairs (B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:12:

GATTGCCTTC TGCAGTAAAT TCTCACACGT GCTTGATTTT CTG    43

(2) INFORMATION FOR SEQ ID NO:13:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:13:

AGGAACTATG GATAT    15

(2) INFORMATION FOR SEQ ID NO:14:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:14:

CTTGCCAATC TGCCT    15

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

( v i ) ORIGINAL SOURCE:

( x i ) SEQUENCE DESCRIPTION: SEQ ID NO:15:

ATGTGATTGC TTCAAGCTTT G   21

What is claimed is:

1. An isolated polynucleotide comprising a polynucleotide which encodes a polypeptide which has the Arginase II activity of the protein which has amino acid sequence shown in SEQ ID NO:2.

2. An isolated polynucleotide comprising a nucleotide sequence encoding the polypeptide of SEQ ID NO:2.

3. The isolated polynucleotide of claim 2 wherein said nucleotide sequence comprises sequence contained in SEQ ID NO:1 which encodes the polypeptide of SEQ ID NO:2.

4. An isolated polynucleotide comprising the nucleotide sequence of SEQ ID NO:1.

5. The isolated polynucleotide which is the polynucleotide of SEQ ID NO:1.

6. An isolated polynucleotide comprising a nucleotide sequence encoding the polypeptide of SEQ ID NO:2 in the cDNA insert deposited at the American Type Culture Collection with Deposit Number 75,656.

7. A polynucleotide sequence which is complementary to any of the isolated polynucleotides in any one of claims 1, 2, 3, 4, 5 and 6.

8. The isolated polynucleotide of any one of claims 1 and 2 which is DNA or RNA.

9. A DNA or RNA molecule comprising an expression vector, wherein said expression vector produces a polypeptide which has Arginase II activity of the protein which has amino acid sequence shown in SEQ ID NO:2.

10. A DNA or RNA molecule comprising an expression vector, wherein said expression vector produces the polypeptide of SEQ ID NO:2.

11. An isolated host cell in culture comprising the DNA or RNA molecule of claim 9.

12. An isolated host cell in culture comprising the DNA or RNA molecule of claim 10.

13. A process for producing a polypeptide which has Arginase II activity of the protein which has amino acid sequence shown in SEQ ID NO:2, comprising: culturing the host cell in culture of claim 11 under conditions sufficient for the production of said polypeptide and recovering said polypeptide from the culture.

14. A process for producing the polypeptide of SEQ ID NO:2, comprising: culturing the host cell in culture of claim 12 under conditions sufficient for the production of said polypeptide and recovering said polypeptide from the culture.

15. A process for producing a cell which produces a polypeptide which has Arginase II activity of the protein which has amino acid sequence shown in SEQ ID NO:2, comprising: transforming or transfecting a host cell with the DNA or RNA molecule of claim 9 such that the host cell, under appropriate culture conditions, procduces said polypeptide.

16. A process for producing a cell which produces the polypeptide of SEQ ID NO:2, comprising: transiorrning or transfecting a host cell with the DNA or RNA molecule of claim 10 such that the host cell, under appropriate culture conditions, produces said polypeptide.

* * * * *